United States Patent [19]

Ohorodnik et al.

[11] 4,261,923

[45] Apr. 14, 1981

[54] PROCESS PERMITTING THE DEPOSITION OF SOLID MATTER IN MIXTURES CONTAINING METHYLDICHLOROPHOSPHANE TO BE INHIBITED

[75] Inventors: Alexander Ohorodnik; Klaus Gehrmann; Eberhard Auer, all of Erftstadt; Stefan Schäfer, Brühl, all of Fed. Rep. of Germany

[73] Assignee: Hoechst Aktiengesellschaft, Fed. Rep. of Germany

[21] Appl. No.: 110,098

[22] Filed: Jan. 7, 1980

[30] Foreign Application Priority Data

Jan. 13, 1979 [DE] Fed. Rep. of Germany ....... 2901298

[51] Int. Cl.[3] .............................................. C07F 9/34
[52] U.S. Cl. ................................................. 260/543 P
[58] Field of Search ..................................... 260/543 P

[56] References Cited

U.S. PATENT DOCUMENTS

| | | |
|---|---|---|
| 3,519,685 | 7/1970 | Baranauckas et al. ........... 260/543 P |
| 3,624,149 | 11/1971 | Bretschneider et al. ......... 260/543 P |
| 4,104,299 | 8/1978 | Ohorodnik et al. ............. 260/543 P |
| 4,104,304 | 8/1978 | Schäfer et al. .................. 260/543 P |

*Primary Examiner*—Helen M. S. Sneed
*Attorney, Agent, or Firm*—Connolly and Hutz

[57] ABSTRACT

The invention relates to a process permitting the deposition of solid matter in mixtures containing methyldichlorophosphane to be avoided. To this end, the mixture is stabilized by admixing it with phosphoric acid or a soluble compound containing at least one acid group selected from phosphoric acid, phosphonic acid, sulfonic acid, phosphonous acid, thiophosphoric acid or dithiophosphoric acid.

3 Claims, No Drawings

PROCESS PERMITTING THE DEPOSITION OF SOLID MATTER IN MIXTURES CONTAINING METHYLDICHLOROPHOSPHANE TO BE INHIBITED

In the production of methyldichlorophosphane from phosphorus trichloride and methane at temperatures higher than 500° C., condensable constituents of the reaction mixture are commonly liquefied in a quenching zone with formation of a crude product which however is very difficult to work up. The difficulties originate from a property which is typical of this particular crude product. On being allowed to stand and more especially on being heated, the crude product is very liable to separate tarry or solid contaminants. Contrary to expectation, these are contaminants which cannot be removed distillatively. In other words, even freshly distilled crude methyldichlorophosphane remains clear for a short while only. Placed in a receptacle, the liquid is rapidly rendered turbid at room temperature, naturally more rapidly at a temperature near its boiling point, and solid matter soon commences depositing on the walls of the receptacle. As a result of this particular behaviour which makes it necessary for the $PCl_3$-conversion to be limited—the tendency of crude methyldichlorophosphane to cause deposition of solid matter increases disproportionately with $PCl_3$-conversion—heat exchanger and pipes become ultimately soiled with depositing material whereby the work-up of the product is rendered considerably more expensive.

The difficulties which have been encountered during the distillative work-up of crude methyldichlorophosphane have already been broadly discussed in German Patent No. 26 31 608 and German Patent Specification "Auslegeschrift" 27 18 391. To avoid these difficulties, it has been suggested that the reaction mixture, after it has been liquefied in a quenching zone, should be admixed with 0.3 to 3 weight % of an organic barium compound or with 0.3 to 5 weight % of a non-ionic surfactant. These are surface-active materials which chiefly prevent produced solid matter from depositing during work-up.

In accordance with our present invention, we have now found that the processes described heretofore for the work-up of crude methyldichlorophosphane can be further improved by admixing the crude product which is to be worked up with a type of stabilizing compounds other than described hereinabove.

The type of stabilizers used in this invention comprise phosphoric acid and all compounds which are soluble in mixtures containing methyldichlorophosphane and contain at least one acid group selected from materials comprised of: phosphoric acid, phosphonic acid, sulfonic acid, phosphonous acid, thiophosphoric acid or dithiophosphoric acid. These compounds, termed stabilizers, combine in themselves the property of obviating the deposition of precipitated solid matter with the property of effectively obviating the formation of solid matter. In other words, freshly distilled clear crude product having one of the above stabilizers admixed therewith is a stabilized methyldichlorophosphane-containing product which remains clear.

The present invention relates more particularly to a process permitting the deposition of solid matter in mixtures containing methyldichlorophosphane to be avoided, which comprises: stabilizing the mixture by admixing it with phosphoric acid or a soluble compound containing at least one acid group selected from phosphoric acid, phosphonic acid, sulfonic acid, phosphonous acid, thiophosphoric acid or dithiophosphoric acid.

A preferred feature of this invention provides for the stabilizer to be used in a proportion of 0.1 to 5 weight %, preferably 0.3 to 3 weight %. A further preferred feature provides for at least one of the compounds of the following formulae to be used as the stabilizer:

$CH_3(CH_2)_7$—$PO(OH)_2$
$CH_3$—$(CH_2)_{11}$—$C_6H_4$—$SO_3H$
$(iso$-$C_{13}H_{27}O)_2P(O)OH$
$C_{13}H_{27}OPO(OH)_2$
$(C_{13}H_{27}O)_2P(O)OH$
$(C_4H_9)_3C_6H_5$—O—$(CH_2CH_2O)_4PO(OH)_2$
$[(C_4H_9)_3C_6H_5$—O—$(CH_2CH_2O)_4]_2P(O)OH$
$C_6H_5$—O—$(CH_2CH_2O)_6PO(OH)_2$
$[C_6H_5$—O—$(CH_2CH_2O)_6]_2P(O)OH$
$CH_3(CH_2)_7CH$=$CH(CH_2)_7CH_2$—O—$(CH_2CH_2O)_5$-$PO(OH)_2$
$[CH_3(CH_2)_7CH$=$CH(CH_2)_7CH_2$—O—$(CH_2CH_2O)_5]_2$-$P(O)OH$
$C_4H_9CH(C_2H_5)$—$CH_2$—O—$PO(OH)_2$
$[C_4H_9CH(C_2H_5)$—$CH_2$—$O]_2P(O)OH$
$(CH_3O)_2P(S)SH$

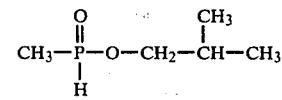

As has been found products containing clear methyldichlorophosphane are easy to work up into pure methyldichlorophosphane. This is a fact of which use can be made in determining the efficiency of a stabilizer.

In testing the stabilizer for its efficiency, use has more particularly been made of the fact that the occurrence of turbidity in a mixture containing methyldichlorophosphane is a stage preliminary to solid matter precipitation, and of the fact that the degree of turbidity caused by mass concentration of discrete particles in a test liquid can be accurately metered physically. The physical principle followed in metering the turbidity is based on the permeability to light of a test liquid, which can be metered with optical instruments. In testing the various stabilizers for their efficiency and influence on the behaviour of products containing methyldichlorophosphane, use was made of a commercially available turbidity meter, model 150, of Electrofact company, Dormagen, Federal Republic of German, which permitted the degree of turbidity to be indicated in ppm.

Experimental work made on the correlation which exists between precipitation of solid matter and degree of turbidity in products containing methyldichlorophosphane have shown that solid matter is liable to commence precipitation from solid matter concentration of 100 ppm upward.

As more fully described in the following Examples, the stabilizing effect of a compound on the behaviour of a mixture containing methyldichlorophosphane, is easy and accurately to determine physically by metering the turbidity.

EXAMPLE 1

3 measuring bottles were used. Each of the three bottles was filled with 100 g of freshly distilled crude methyldichlorophosphane which was composed of:

73.0 weight % of phosphorus trichloride,
4.0 weight % of carbon tetrachloride,
2.0 weight % of chloroform,
17.0 weight % of methyldichlorophosphane, the balance being dimethylchlorophosphane and unidentified components. The turbidity was metered as follows: in first measuring bottle, after 1 hour; in second bottle, after 50 hours; and in third bottle, after boiling for 5 minutes under reflux. The results obtained are indicated in the Table hereinafter.

EXAMPLE 2

100 g of freshly distilled crude methyldichlorophosphane with the composition indicated in Example 1 was admixed in each particular case with 0.5 g of dodecylbenzenesulfonic acid $CH_3-(CH_2)_{11}-C_6H_4SO_3H$ and treated as described in Example 1. The results obtained are indicated in the following Table, for the purpose of comparison.

EXAMPLES 3 to 12

The following substances were evaluated under analogous conditions:
EXAMPLE 3: Phosphoric acid $PO(OH)_3$
EXAMPLE 4: Octanephosphonic acid $CH_3(CH_2)_7PO(OH)_2$
EXAMPLE 5: Di-iso-tridecylphosphoric acid ester $(iso-C_{13}H_{27}O)_2P(O)OH$
EXAMPLE 6: Mixture of mono- and di-tridecylphosphoric acid esters $C_{13}H_{27}OPO(OH)_2$ and $(C_{13}H_{27}O)_2P(O)OH$
EXAMPLE 7: Mixture of mono- and diphosphoric acid esters of tributylphenoltetraglycolether $(C_4H_9)_3C_6H_5-O-(CH_2CH_2O)_4PO(OH)_2$ and $[(C_4H_9)_3C_6H_5-O-(CH_2CH_2O)_4]_2P(O)OH$
EXAMPLE 8: Mixture of mono- and diphosphoric acid esters of phenylhexaglycolether $C_6H_5-O-(CH_2CH_2O)_6PO(OH)_2$ and $[C_6H_5-O-(CH_2CH_2O)_6]_2P(O)OH$
EXAMPLE 9: Mexture of mono- and diphosphoric acid esters of oleylpentaglycolether $CH_3(CH_2)_7CH=CH(CH_2)_7CH_2-O-(CH_2CH_2O)_5-PO(OH)_2$ and $[CH_3(CH_2)_7CH=CH(CH_2)_7CH_2-O-(CH_2CH_2O)_5]_2P(O)OH$
EXAMPLE 10: Mixture of mono- and di-hexyl(β-ethyl)phosphoric acid esters $C_4H_9CH(C_2H_5)-CH_2-O-PO(OH)_2$ and $[C_4H_9CH(C_2H_5)-CH_2-O]_2P(O)OH$
EXAMPLE 11: 0,0-dimethyldithiophosphoric acid $(CH_3O)_2P(S)SH$
EXAMPLE 12: Methanephosphonous acid isobutylester $$CH_3-\underset{\underset{H}{|}}{\overset{\overset{O}{\|}}{P}}-O-CH_2-\underset{\underset{}{|}}{\overset{\overset{CH_3}{|}}{CH}}-CH_3$$

TABLE

| Ex. No. | | ppm solid matter after 1 hour | ppm solid matter after 50 hours | ppm solid matter 5 minutes after boiling |
|---|---|---|---|---|
| 1 | without addent | 100 | 1000 | 1000 |
| 2 | | 10 | 10 | 10 |
| 3 | | 10 | 10 | 10 |
| 4 | | 10 | 100 | 10 |
| 5 | | 10 | 10 | 10 |
| 6 | | 10 | 10 | 10 |
| 7 | | 50 | 50 | 50 |
| 8 | | 10 | 100 | 10 |
| 9 | | 10 | 10 | 10 |
| 10 | | 10 | 300 | 100 |
| 11 | | 50 | 50 | 100 |
| 12 | | 50 | 50 | 100 |

We claim:
1. A process of inhibiting the deposition of solid matter in mixtures containing methyldichlorophosphane, which comprises: stabilizing the mixture by admixing it with phosphoric acid or a soluble compound containing at least one acid group selected from phosphoric acid, phosphonic acid, sulfonic acid, phosphonous acid, thiophosphoric acid or dithiophosphoric acid.
2. A process as claimed in claim 1, wherein the stabilizer is used in a proportion of 0.1 to 5 weight %.
3. A process as claimed in claim 1, wherein at least one of the following compounds is used as the stabilizer:
$CH_3(CH_2)_7-PO(OH)_2$
$CH_3-(CH_2)_{11}-C_6H_4-SO_3H$
$iso-C_{13}H_{27}O)_2P(O)OH$
$C_{13}H_{27}OPO(OH)_2$
$C_{13}H_{27}O)_2P(O)OH$
$C_4H_9)_3C_6H_5-O-(CH_2CH_2O)_4PO(OH)_2$
$[(C_4H_9)_3C_6H_5-O-(CH_2CH_2O)_4]_2P(O)OH$
$C_6H_5-O-(CH_2CH_2O)_6PO(OH)_2$
$[C_6H_5-O-(CH_2CH_2O)_6]_2P(O)OH$
$CH_3(CH_2)_7CH=CH(CH_2)_7CH_2-O-(CH_2CH_2O)_5-PO(OH)_2$
$[CH_3(CH_2)_7CH=CH(CH_2)_7CH_2-O-(CH_2CH_2O)_5]_2P(O)OH$
$C_4H_9CH(C_2H_5)-CH_2-O-PO(OH)_2$
$[C_4H_9CH(C_2H_5)-CH_2-O]_2P(O)OH$
$(CH_3O)_2P(S)SH$

$$CH_3-\underset{\underset{H}{|}}{\overset{\overset{O}{\|}}{P}}-O-CH_2-\underset{\underset{}{|}}{\overset{\overset{CH_3}{|}}{CH}}-CH_3$$

* * * * *